United States Patent [19]

Jäger et al.

[11] 4,322,442

[45] Mar. 30, 1982

[54] COMBATING FUNGI WITH 1-HALO-1-PROPYN-3-OLS

[75] Inventors: Gerhard Jäger, Wuppertal; Erich Klauke, Odenthal; Wilhelm Brandes, Leichlingen; Paul-Ernst Frohberger, Leverkusen, all of Fed. Rep. of Germany

[73] Assignee: Bayer Aktiengesellschaft, Leverkusen, Fed. Rep. of Germany

[21] Appl. No.: 184,694

[22] Filed: Sep. 8, 1980

Related U.S. Application Data

[63] Continuation of Ser. No. 964,543, Nov. 29, 1978.

[30] Foreign Application Priority Data

Dec. 15, 1977 [DE] Fed. Rep. of Germany ....... 2756031

[51] Int. Cl.³ .................... A01N 31/14; A01N 31/04
[52] U.S. Cl. .................................. 424/341; 424/345; 424/285; 424/275; 424/273 P; 568/809; 568/641; 568/705; 568/807; 568/637; 568/586; 568/713; 568/642; 424/263; 424/337; 424/304; 424/330; 568/45; 568/51; 260/465 F; 564/315; 549/78; 260/347.8; 546/343; 548/378
[58] Field of Search .............. 568/809, 641, 705, 807, 568/637, 586, 713; 424/340, 341, 345

[56] References Cited

U.S. PATENT DOCUMENTS 2,711,384  6/1955  Darley ................................. 424/345
2,895,871  7/1959  Entemann ........................ 424/345

FOREIGN PATENT DOCUMENTS 1404792   5/1965  France ................... 568/813
42-11734  4/1967  Japan ..................... 568/584
300839   11/1954  Switzerland ............ 424/345

*Primary Examiner*—Bernard Helfin
*Attorney, Agent, or Firm*—Sprung, Felfe, Horn, Lynch & Kramer

[57] ABSTRACT

1-Halo-1-propyn-3-ols of the formula

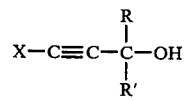

in which

R is optionally substituted phenyl, pyridyl, furyl, thienyl or pyrazolyl,
R' is optionally substituted phenyl, and
X is halogen, which possess fungicidal properties.

5 Claims, No Drawings

COMBATING FUNGI WITH 1-HALO-1-PROPYN-3-OLS

This is a continuation of application Ser. No. 964,543, filed Nov. 29, 1978, now pending.

The present invention relates to and has for its objects the provision of particular new 1-halo-1-propyn-3-ols which possess insecticidal properties, active compositions in the form of mixtures of such compounds with solid and liquid dispersible carrier vehicles, and methods for producing such compounds and for using such components in a new way especially for combating pests, e.g. fungi, with other and further objects becoming apparent from a study of the within specification and accompanying examples.

It has already been disclosed that azolylalkynes, such as, for example, 3-imidazol-1-yl-3-isopropyl-3-phenyl-1-propyne, 1,1-diphenyl-1-imidazol-1-yl-2-octyne or 1-bromo-3,3-diphenyl-3-imidazol-1-yl-1-propyne, have good fungicidal properties (see U.S. Pat. No. 3,832,466 issued Aug. 27, 1974). However, their activity is not always completely satisfactory, especially when low amounts and concentrations are used. In addition, their plant tolerance and seed tolerance when used as seed dressings are not always completely satisfactory.

The present invention now provides, as new compounds, the 1-halo-1-propyn-3-ols of the general formula

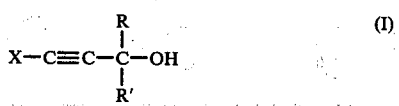

in which

R represents phenyl, pyridyl, furyl, thienyl or pyrazolyl, the radicals mentioned being optionally substituted, R' represents optionally substituted phenyl and X represents halogen.

They have powerful fungicidal properties.

Preferably, R represents phenyl which optionally carries one or more substitutents selected from halogen, alkyl with 1 to 4 carbon atoms, alkoxy and alkylthio with in either case 1 or 2 carbon atoms, haloalkyl and haloalkoxy with in either case up to 2 carbon atoms and up to 5 halogen atoms (especially fluorine atoms and chlorine atoms), amino, cyano, nitro, phenyl and phenoxy, the last two radicals being optionally substituted by halogen or alkyl with 1 to 2 carbon atoms, or R represents a pyridyl, furyl, thienyl or pyrazolyl radical which optionally carries one or more substituents selected from halogen and alkyl with 1 or 2 carbon atoms; R' represents phenyl which optionally carries one or more substituents selected from halogen, alkyl with 1 to 4 carbon atoms, alkoxy and alkylthio with in either case 1 or 2 carbon atoms, haloalkyl and haloalkoxy with in either case up to 2 carbon atoms and up to 5 halogen atoms (especially fluorine atoms and chlorine atoms), amino, cyano, nitro, phenyl and phenoxy, the last two radicals being optionally substituted by halogen or alkyl with 1 to 2 carbon atoms; and X represents bromine or iodine.

Surprisingly, the 1-halo-1-propyn-3-ols according to the invention exhibit a considerably higher fungicidal action than the azolylalkynes known from the state of the art, which chemically and from the point of view of their action are closely related compounds. The active compounds according to the invention thus represent an enrichment of the art.

The present invention also provides a process for the preparation of a 1-halo-1-propyn-3-ol of the formula (I) in which a 1-propyn-3-ol of the general formula

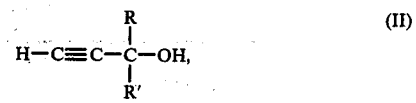

in which R and R' have the meanings stated above, is reacted with a halogen in the presence of an aqueous alkali metal hydroxide solution and in the presence of a diluent.

If 3-phenyl-3-pyridin-4-yl-1-propyn-3-ol and iodine are used as starting materials, the course of the reaction can be represented by the equation which follows:

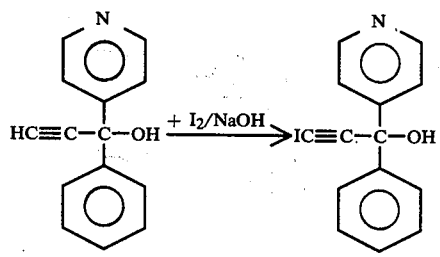

The starting materials of the formula (II) are known and can be prepared in a known manner (see DT-OS (German Published Specification) No. 2,438,462 and the literature references cited therein). They are obtained, for example, by the ethynylation of corresponding ketones, by cooling liquid ammonia to −60° to −70° C. and passing acetylene in, metallic sodium or potassium being added in several small portions to the liquid ammonia; thereafter, the ketone to be ethynylated is allowed to run slowly, in the presence of a solvent if appropriate, into this heterogeneous reaction mixture. After the reaction has ended, the liquid ammonia is allowed to evaporate off overnight and the end products are isolated in the customary manner. The ethynylation can also be carried out by reacting the corresponding ketone with acetylene in the presence of an alkali metal derivative of a tertiary alkanol, in an aprotic organic solvent (see also the preparative examples hereinbelow).

Examples of the 1-propyn-3-ols of the formula (II) to be used according to the invention as starting materials are given in the following table:

TABLE 1

$$H-C\equiv C-\underset{\underset{R'}{|}}{\overset{\overset{R}{|}}{C}}-OH \quad (II)$$

| R | R' | Melting point (°C.) or boiling point (°C./mm Hg) |
|---|---|---|
| 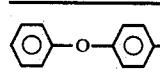 |  | viscous oil |

TABLE 1-continued $$H-C\equiv C-\underset{\underset{R'}{|}}{\overset{\overset{R}{|}}{C}}-OH \quad (II)$$

| R | R' | Melting point (°C.) or boiling point (°C./mm Hg) |
|---|---|---|
| 4-phenoxyphenyl | 4-chlorophenyl | 86–87 |
| 4-phenoxyphenyl | 4-methylphenyl (via 2-chlorophenyl) | 78–79 |
| 4-phenoxyphenyl | 2-chlorophenyl | viscous oil |
| pyridin-3-yl | phenyl | 165–166 |
| pyridin-3-yl | 4-methylphenyl | 191–93 |
| pyridin-4-yl | phenyl | 140–41 |
| pyridin-2-yl | 4-methylphenyl | 144–45 |
| pyridin-2-yl | phenyl | 65–66 |
| phenyl | phenyl | 48,5 |
| phenyl | 4-nitrophenyl | 87–88 |
| biphenyl | 2-chlorophenyl | 123–24 |
| biphenyl | 3-methyl-2-chlorophenyl | 104–06 |
| biphenyl | 2-chlorophenyl | 126–28 |
| phenyl | 2,4-dichlorophenyl | 85–86 |
| 1,3-dimethylpyrazol-5-yl | phenyl | 111–12 |
| phenyl | 2,3-difluorophenyl | 126/0.1 |
| phenyl | 4-fluorophenyl | 118–22/0.1 |
| phenyl | 2-fluorophenyl | 118–21/0.1 |
| phenyl | 2,4-difluorophenyl | 140–45/0.05 |
| phenyl | 4-trifluoromethoxyphenyl | 130/0.05 |
| phenyl | 2-chloro-4-trifluoromethoxyphenyl | 125–30/0.07 |
| 4-chlorophenyl | biphenyl | 106–07 |
| furan-2-yl | 2-chlorophenyl | 146–48/0.08 |
| thien-2-yl | phenyl | 130–36/0.15 |

Bromine or iodine are preferably used as the halogens for the reaction according to the invention.

Preferred diluents for the reaction according to the invention are protic solvents, especially alcohols, such as methanol, ethanol, propanol and isopropanol, and glycol monomethyl ether. If appropriate, the reaction can be carried out in mixtures of these solvents with other solvents, such as, for example, with water or with organic amines, such as pyridine, quinoline or picolines.

The reaction according to the invention is carried out in the presence of an alkali metal hydroxide. Aqueous solutions of sodium hydroxide or potassium hydroxide are preferably used for this.

The reaction temperatures in the process according to the invention can be varied within a substantial range. In general, the reaction is carried out at from 0° to 50° C., preferably at from 20° to 30° C.

In carrying out the process according to the invention, either the halogen and the aqueous alkali metal hydroxide solution are simultaneously added to the compound of the formula (II), or a mixture of the alkali metal hydroxide solution and the halogen is immediately added to this compound. Equimolar amounts of the reactants are preferably used. In order to isolate the compound of the formula (I), water is added to the reaction mixture and the mixture is worked up in the customary manner.

Particularly active compounds of the formula (I) which may be mentioned (in addition to those of the preparative examples) are the following: 1-iodo-3-phenyl-3-pyridin-3-yl-1-propyn-3-ol, 1-bromo-3-(4-chlorophenyl)-3-pyridin-4-yl-1-propyn-3-ol, 3-(4-chlorophenyl)-1-iodo-3-pyridin-4-yl-1-propyn-3-ol, 1-bromo- 3-(2,4-dichlorophenyl)-3-pyridin-4-yl-1-propyn-3-ol,
3-(2,4-dichlorophenyl)-1-iodo-3-pyridin-4-yl-1-propyn-3-ol, 1-bromo-3-(4-fluorophenyl)-3-pyridin-4-yl-1-propyn-3-ol, 3-(4-fluorophenyl)-1-iodo-3-pyridin-4-yl-1-propyn-3-ol, 3,3-bis-(4-chlorophenyl)-1-bromo-1-propyn-3-ol, 3,3-bis-(4-chlorophenyl)-1-iodo-1-propyn-3-ol, 1-bromo-3-(4-chlorophenyl)-3-(2,4-dichlorophenyl)-1-propyn-3-ol, 3-(4-chlorophenyl)-3-(2,4-dichlorophenyl)-1-iodo-1-propyn-3-ol, 1-bromo-3-(2-chlorophenyl)-3-(4-chlorophenyl)-1-propyn-3-ol, 3-(2-chlorophenyl)-3-(4-chlorophenyl)-1-iodo-1-propyn-3-ol, 1-bromo-3-(2-chlorophenyl)-3-(2,4-dichlorophenyl)-1-propyn-3-ol, 3-(2-chlorophenyl)-3-(2,4-dichlorophenyl)-1-iodo-1-propyn-3-ol, 1-bromo-3-(3-chlorophenyl)-3-(2,4-dichlorophenyl)-1-propyn-3-ol, 3-(3-chlorophenyl)-3-(2,4-dichlorophenyl)-1-iodo-1-propyn-3-ol, 1-bromo-3-(3-chlorophenyl)-3-(4-chlorophenyl)-1-propyn-3-ol, 3-(3-chlorophenyl)-3-(4-chlorophenyl)-1-iodo-1-propyn-3-ol, 1-bromo-3-(4-bromophenyl)-3-(4-chlorophenyl)-1-propyn-3-ol, 3-(4-bromophenyl)-3-(4-chlorophenyl)-1-iodo-1-propyn-3-ol, 1-bromo-3-(4-bromophenyl)-3-(2-chlorophenyl)-1-propyn-3-ol and 3-(4-bromophenyl)-3-(2-chlorophenyl)-1-iodo-1-propyn-3-ol.

The active compounds according to the invention exhibit a powerful fungitoxic action. They do not damage crop plants in the concentrations required for combating fungi. For these reasons they are suitable for use as plant protection agents for combating fungi. Fungitoxic agents are employed in plant protection for combating Plasmodiophoromycetes, Oomycetes, Chytridiomycetes, Zygomycetes, Ascomycetes, Basidiomycetes and Deuteromycetes.

The active compounds according to the invention have a broad spectrum of action and can be used against parasitic fungi which infect above-ground parts of plants or attack the plants through the soil, as well as against seed-borne pathogens. They develop a particularly good activity against parasitic fungi on above-ground parts of plants.

As plant protection agents, the active compounds according to the invention can be used with particularly good success for combating *Phytophthora infestans* (brown rot of tomatoes) and species of Venturia, for example against the apple scab causative organism (*Fusicladium dendriticum*); they can furthermore also be used for combating cereal diseases, such as cereal rust and bunt of wheat. Good effects are also achieved in combating *Pyricularia oryzae* in rice.

As plant protection agents, the active compounds according to the invention can be used for the treatment of seed or soil and for the treatment of above-ground parts of plants.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanide dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations as a mixture with other active compounds, such as fungicides, insecticides, acaricides, nematicides, herbicides, bird repellents, growth factors, plant nutrients and agents for improving the soil structure.

The active compounds can be used as such, as their formulations or as the use forms prepared therefrom by further dilution, such as ready-to-use solutions, emulsions, suspensions, powders, pastes and granules. They may be used in the customary manner, for example by watering, spraying, atomising, dusting, scattering, dry dressing, moist dressing, wet dressing, slurry dressing or encrusting.

Especially when used as leaf fungicides, the active compound concentrations in the use forms can be varied within a substantial range. They are, in general, from 0.1 to 0.00001 percent by weight, preferably from 0.05 to 0.0001 percent.

In the treatment of seed, amounts of active compound of 0.001 to 50 g, preferably 0.01 to 10 g, are generally employed per kilogram of seed.

In appropriate use concentrations, the active compounds according to the invention also exhibit an acaricidal action.

The present invention also provides a fungicidal composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

The following examples illustrate the preparation of the novel compounds of the invention.

EXAMPLE 1

(a) Preparation of the starting material

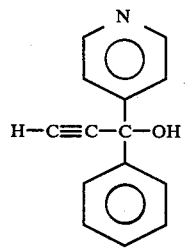

Acetylene was passed into a suspension of 174 g (1.55 mol) of potassium tert.-butylate in 750 ml of tetrahydrofuran for about 30 minutes. 198 g (1.08 mol) of 4-benzoylpyridine in 400 ml of tetrahydrofuran were added dropwise to this reaction mixture, acetylene being simultaneously passed in for about a further hour. The mixture was subsequently stirred for 30 minutes, dilute hydrochloric acid was added, the salt which had precipitated was filtered off and the organic phase of the filtrate was separated off. This phase was concentrated in vacuo. The solid residue was triturated with water and the solid was filtered off and washed with methanol/- water (1:1). 170 g (75% of theory) of 3-phenyl-3-pyridin-4-yl-1-propyn-3-ol of melting point 165°-66° C. were obtained.

(b)

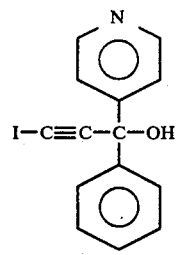

(1)

50.8 g (0.2 mol) of iodine were gradually introduced into a suspension of 42 g (0.2 mol) of 3-phenyl-3-pyridin-4-yl-1-propyn-3-ol in 500 ml of methanol at room temperature, while simultaneously adding 80 ml of concentrated sodium hydroxide solution dropwise. An almost clear solution was thereby obtained. After stirring the solution at room temperture for three hours, it was diluted with a large amount of water and the crystals which had separated out were filtered off, washed with water and dried in vacuo. After recrystallization from methanol, 53 g (79.2% of theory) of 1-iodo-3-phenyl-3-pyridin-4-yl-1-propyn-3-ol were obtained as colorless crystals of melting point 175° C. (decomposition).

EXAMPLE 2

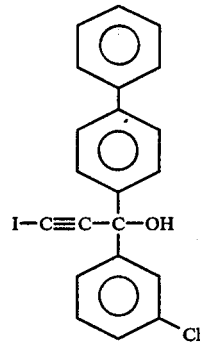

(2)

40 ml of concentrated sodium hydroxide solution and 25.4 g (0.1 mol) of iodine were simultaneously introduced into a solution of 31.9 g (0.1 mol) of 3-(4-biphenylyl)-3-(3-chlorophenyl)-1-propyn-3-ol in 350 ml of methanol at 20° C., with slight external cooling and while stirring. The mixture was stirred for three hours and filtered to remove a slight turbidity and the filtrate was stirred into 1,000 ml of water. The reaction product thereby separated out as a semi-solid mass. The supernatant liquid was decanted, the residue was taken up in ethyl acetate and the solution was washed several times with 100 ml of water each time and dried over sodium sulphate. Thereafter, it was concentrated by distilling off the solvent in vacuo, and the oily residue was dissolved in a little ether. After adding petroleum ether, crystallization occurred. 25.3 g (56.9% of theory) of 3-(4-biphenylyl)-3-(3-chlorophenyl)-1-iodo-1-propyn-3-ol were obtained as colorless crystals of melting point 99°–100° C.

EXAMPLE 3

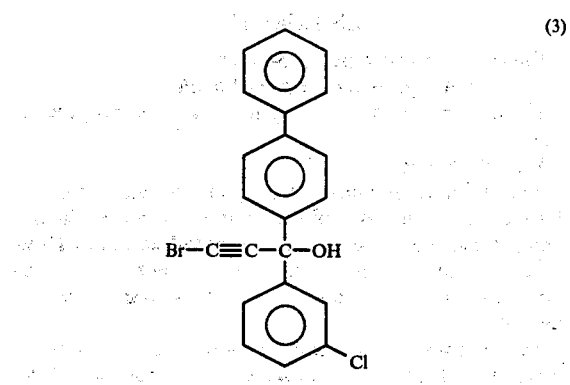
(3)

8.2 ml (0.16 mol) of bromine were stirred into 129 ml (0.32 mol) of 10% strength sodium hydroxide solution at 0° to 5° C. 44.6 g (0.14 mol) of 3-(4-biphenylyl)-3-(3-chlorophenyl)-1-propyn-3-ol in 150 ml of pyridine were added dropwise to this solution at room temperature, the temperature of the reaction mixture rising to 30° C. The mixture was left to stand at room temperature for 24 hours and the crystals which had separated out were filtered off and rinsed thoroughly with water. After drying and recrystallizing from petroleum ether/ether, 43 g (77.2% of theory) of 1-bromo-3-(4-diphenylyl)-3-(3-chlorophenyl)-1-propyn-3-ol of melting point 106°–107° C. were obtained.

The compounds of Table 2 which follows were obtained in an analogous manner.

TABLE 2

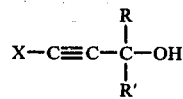

| Compound No. | R | R' | X | Melting point (°C.) or refractive index |
|---|---|---|---|---|
| 4 | 4-biphenylyl | 3-methylphenyl | I | 137–39 |
| 5 | 4-biphenylyl | 3-methylphenyl | Br | 131–32 |
| 6 | 4-biphenylyl | 3-chlorophenyl | I | viscous oil |
| 7 | 3-chlorophenyl | 4-biphenylyl | Br | 77–79 (x pyridine) |
| 8 | 4-phenoxyphenyl | 3-chlorophenyl | I | 104–05 |
| 9 | 4-phenoxyphenyl | 3-chlorophenyl | I | viscous oil |
| 10 | 4-phenoxyphenyl | 3-chlorophenyl | Br | 95–96 |
| 11 | 2-pyridyl | phenyl | Br | 107–08 |
| 12 | 2-pyridyl | phenyl | I | 86–87 |
| 13 | phenyl | phenyl | I | 106–07 |
| 14 | 4-pyridyl | phenyl | Br | 166–67 |
| 15 | phenyl | 4-nitrophenyl | I | 116–18 |
| 16 | 4-phenoxyphenyl | 2-chlorophenyl | Br | viscous oil |
| 17 | 4-phenoxyphenyl | 4-chlorophenyl | I | viscous oil |
| 18 | 4-phenoxyphenyl | 3-methylphenyl | I | 82–83 |
| 19 | 4-phenoxyphenyl | 4-chlorophenyl | Br | viscous oil |
| 20 | 4-phenoxyphenyl | 3-methylphenyl | Br | viscous oil |
| 21 | 4-pyridyl | 4-methylphenyl | I | 179–80 (decomposition) |
| 22 | 4-pyridyl | 4-methylphenyl | Br | 189 (decomposition) |
| 23 | phenyl | 3-fluorophenyl | I | 81–82 |
| 24 | phenyl | 3-fluorophenyl | Br | $n_D^{20}$: 1.6040 |
| 25 | phenyl | 3,4-difluorophenyl | I | $n_D^{20}$: 1.6098 |
| 26 | phenyl | 3,4-difluorophenyl | Br | $n_D^{20}$: 1.5845 |
| 27 | phenyl | 4-trifluoromethoxyphenyl | I | $n_D^{20}$: 1.5697 |

TABLE 2-continued $$X-C\equiv C-\underset{\underset{R'}{|}}{\overset{\overset{R}{|}}{C}}-OH$$

| Compound No. | R | R' | X | Melting point (°C.) or refractive index |
|---|---|---|---|---|
| 28 |  | 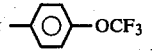—OCF₃ | Br | $n_D^{20}: 1.5497$ |
| 29 |  | 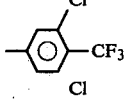—CF₃ (Cl) | I | $n_D^{20}: 1.5860$ |
| 30 |  | 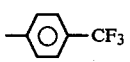—CF₃ (Cl) | Br | $n_D^{20}: 1.5683$ |
| 31 |  | 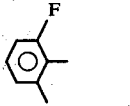 (F, F) | I | 93–95 |
| 32 |  | 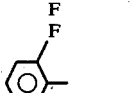 (F, F) | Br | 60–61 |
| 33 |  |  | Br | 60–62 |
| 34 | 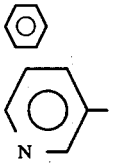 | 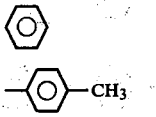—CH₃ | I | 148–50 |
| 35 | 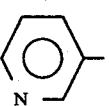 | 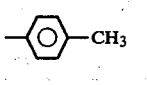—CH₃ | Br | 152 (decomposition) |

The fungicidal activity of the compounds of this invention is illustrated by the following examples:

EXAMPLE 4

Phytophthora test (tomatoes)/protective
Solvent: 4.7 parts by weight of acetone
Emulsifier: 0.3 part by weight of alkylaryl polyglycol ether
Water: 95.0 parts by weight The amount of the active compound required for the desired concentration of the active compound in the spray liquid was mixed with the stated amount of solvent and the concentrate was diluted with the stated amount of water which contained the stated amount of emulsifier.

Young tomato plants with 2 to 4 foliage leaves were sprayed with the spray liquid until dripping wet. The plants remained in a greenhouse for 24 hours at 20° C. and at a relative atmospheric humidity of 70%. The tomato plants were then inoculated with an aqueous spore suspension of *Phytophthora infestans*. The plants were brought into a moist chamber with an atmospheric humidity of 100% and a temperature of 18° to 20° C.

After 5 days the infection of the tomato plants was determined. Compounds 6, 12, 13, 21, 23, 25, 27, 29 and 31 exhibited a very good action which was distinctly superior to that of the compounds known from the prior art.

EXAMPLE 5

Fusicladium test (apple)/protective
Solvent: 4.7 parts by weight of acetone
Emulsifier: 0.3 part by weight of alkylaryl polyglycol ether
Water: 95.0 parts by weight The amount of active compound required for the desired concentration of the active compound in the spray liquid was mixed with the stated amount of solvent and the concentrate was diluted with the stated amount of water which contained the stated amount of emulsifier.

Young apple seedlings in the 4 to 6 leaf stage were sprayed with the spray liquid until dripping wet. The plants remained in a greenhouse for 24 hours at 20° C. and at a relative atmospheric humidity of 70%. They were then inoculated with an aqueous conidium suspension of the apple scab causative organism (*Fusicladium dendriticum*) and incubated for 18 hours in a humidity chamber at 18° to 20° C. and at a relative atmospheric humidity of 100%.

The plants were then brought into a greenhouse again for 14 days.

15 days after inoculation, the infection of the seedlings were determined. Compounds 2, 8, 12, 13, 23, 25, 27 and 29 exhibited a very good action which was distinctly superior to that of the compounds known from the prior art.

EXAMPLE 6

Shoot treatment test/cereal rust/protective (leaf-destructive mycosis)

To produce a suitable preparation of active compound, 0.25 part by weight of active compound was taken up in 25 parts by weight of dimethylformamide and 0.06 part by weight of alkylaryl polyglycol ether, and then 975 parts by weight of water were added. The concentrate was diluted with water to the desired final concentration of the spray liquor.

To test the protective activity, one-leaved young wheat plants of the Michigan Amber variety were inoculated with a uredospore suspension of *Puccinia recondita* in 0.1% strength aqueous agar. After the spore suspension had dried on, the wheat plants were sprayed with the preparation of active compound until dew-moist and were placed, for incubation, in a greenhouse for 24 hours at about 20° C. and 100% atmospheric humidity.

After 10 days' dwell time of the plants at a temperature of 20° C. and 80–90% atmospheric humidity, the occurrence of rust pustules on the plants was evaluated. The degree of infection was expressed as a percentage of the infection of the untreated control plants. 0% denoted no infection and 100% denoted the same degree of infection as in the case of the untreated control. The more active the compound, the lower was the degree of infection.

In this test, for example, compounds 12, 13, 23, 25, 27 and 31 exhibited a very good action which was distinctly superior to that of the compounds known from the prior art.

EXAMPLE 7

Seed dressing test/bunt of wheat (seed-borne mycosis)

To produce a suitable dry dressing, the active compound was extended with a mixture of equal parts by weight of talc and kieselguhr to give a finely powdered mixture with the desired concentration of the active compound.

Wheat seed was contaminated with 5 g of the chlamydospores of *Tilletia caries* per kg of seed. To apply the dressing, the seed was shaken with the dressing in a closed glass flask. The seed, on moist loam under a cover of a layer of muslin and 2 cm of moderately moist compost soil, was exposed to optimum germination conditions for the spores for 10 days at 10° C. in a refrigerator.

The germination of the spores on the wheat grains, each of which was contaminated with about 100,000 spores, was subsequently determined microscopically. The smaller the number of spores which had generated, the more effective was the active compound.

In this test, for example, compounds 1, 12 and 13 exhibited a very good action which was distinctly superior to that of the compounds known from the prior art.

It will be appreciated that the instant specification and examples are set forth by way of illustration and not limitation, and that various modifications and changes may be made without departing from the spirit and scope of the present invention.

What is claimed is:

1. A method of combating plant pathogenic fungi which comprises applying to plants, seeds or soil a fungicidally effective amount of a 1-halo-1-propyn-3-ol of the formula 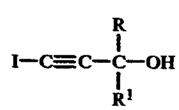 in which R and $R^1$ each independently is phenyl optionally carrying at least one substituent selected from halogen, alkyl with 1 to 4 carbon atoms, methoxy, ethoxy, haloalkyl, and haloalkoxy with 1 or 2 carbon atoms and up to 5 halogen atoms, nitro, and phenyl and phenoxy optionally substituted by halogen or alkyl with 1 or 2 carbon atoms; with the proviso that at least one of R and $R^1$ is substituted phenyl.

2. The method according to claim 1, wherein a such compound is 3-phenyl-3-(2-fluorophenyl)-1-iodo-1-propyn-3-ol of the formula 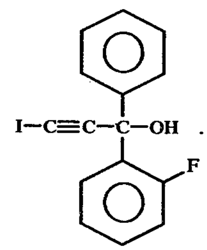 3. The method according to claim 1, wherein such compound is 3-phenyl-3-(2,4-difluorophenyl)-1-iodo-1-propyn-3-ol of the formula 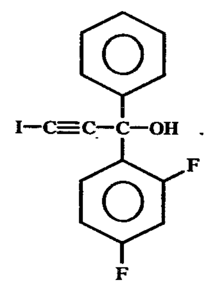 4. The method according to claim 1, wherein such compound is 3-phenyl-3-(4-trifluoromethoxyphenyl)-1-iodo-1-propyn-3-ol of the formula 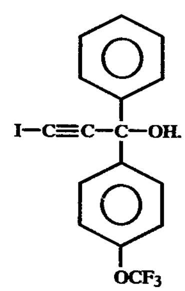 5. The method according to claim 1, wherein such compound is 3-phenyl-3-(3-chloro-4-trifluoromethyl-phenyl)-1-iodo-1 -propyn-3-ol of the formula

* * * * *